United States Patent [19]

Thimel-Baumer

[11] Patent Number: 4,541,953
[45] Date of Patent: Sep. 17, 1985

[54] PREPARATION OF ANTI-T-LYMPHOCYTE GLOBULIN

[76] Inventor: Heidi Thimel-Baumer, Candidstrasse 18, 8000 Munchen 90, Fed. Rep. of Germany

[21] Appl. No.: 582,030

[22] Filed: Feb. 21, 1984

Related U.S. Application Data

[63] Continuation-in-part of Ser. No. 347,502, Feb. 9, 1982, abandoned.

[30] Foreign Application Priority Data

Feb. 12, 1981 [DE] Fed. Rep. of Germany ....... 3105150

[51] Int. Cl.$^4$ ...................... C07G 7/00; A61K 39/395
[52] U.S. Cl. ............................. 260/112 B; 260/112 R; 424/85; 424/88; 435/68; 435/172.2; 435/240; 435/241; 436/548; 436/543
[58] Field of Search ...................... 260/112 B, 112 R; 435/68, 240, 241, , 172, 448, 172.2; 424/85, 88

[56] References Cited

U.S. PATENT DOCUMENTS

| 4,361,549 | 11/1982 | Kung et al. | 260/112 R |
| 4,361,550 | 11/1982 | Kung et al. | 260/112 R |
| 4,363,799 | 12/1982 | Kung et al. | 260/112 R |
| 4,364,933 | 12/1982 | Kung et al. | 260/112 R |

FOREIGN PATENT DOCUMENTS

0030815  6/1981  European Pat. Off. .

OTHER PUBLICATIONS

Vol. 20: Immunological Diagnosis of Leukemias and Lymphomas, "Characterization of 'T' and 'Non-T' Cell Lines Established from Children with Acute Lymphoblastic Leukemia and Non–Hodgkin Lymphoma After Leukemic Transformation", 1977, pp. 265-269.
Thomas et al, "T Cell-Specific Activity in Rabbit Anti--Human Thymocyte Globulin", 1978, pp. 97-102.
Schneider, et al., "Characterization of EBV–Genome Negative 'Null' and 'T' Cell Lines Derived from Children with Acute Lymphoblastic Leukemia and Leukemic Transformed Non-Hodgkin Lymphoma", 1977, pp. 621-626.
Schwenk et al, "Difference in Distribution and Dynamics of Cell-Markers on T-Lymphoblasts Compared to T-Lymphocytes", 1976, pp. 215-219.
Rodt et al, "Characterization of Antigens on Leukemic Cells and Cell Lines Using Specific Heterologous Antisera", 1977, pp. 573-578.
Schwenk H. U. et al, "Detection of Lymphoblasts in Remission Bone Marrow Using Immunological Markers", 1977, pp. 700-704.
Schwenk et al, "Binding of Lectins to Leukemic Cell Lines", 1980, pp. 7-15.
Minowada et al, "Marker Profiles of Human Leukemia and Lymphoma Cell Lines", 1981, pp. 91-100.
Richard W. Smith et al, "The Immunosuppressive Potency of Anti–Lymphocyte Serum is Related to Activity Against Human Thymic Lymphocyte-Specific Antigens", 1974; pp. 503-507.
Gillis et al., "Biochemical and Biological Characterization of Lymphocyte Regulatory Molecules", 1980, pp. 1709-1719.
Lakow et al, "Human T Cell Hybridomas Specific for Epstein Barr Virus-Infected B Lymphocytes", 1983, pp. 169-172.
Mayer et al, "Human T Cell Hybridomas Secreting Factors for IgA-Specific help, Polyclonal B Cell Activation, and B Cell Proliferation", 1982, pp. 1860-1865.
DeFreitas et al, "Antigen-Specific Human T-Cell Hybridomas with Helper Activity (Mutant T-Cell Lines/-Cell Fusion/Tetanus Toxoid/Interleukin 2)", 1982, pp. 6646-6650.
Cassel et al, "Phorbol Ester Modulation of T-Cell Antigens in the Jurkat Lymphoblastic Leukemia Cell Line", 1983, pp. 4582-4586.
Pawelec et al, "Constitutive Interleukin 2 Production by the Jurkat Human Leukemic T Cell Line", 1982, pp. 387-392.
Hans–Ulrich Schwenk et al, "Cell Cycle Dependency of a T-Cell Marker on Lymphoblasts", 1975, pp. 299-306.
Kenneth Sell, et al; "Evaluation of Human Cultured Lymphoblasts as a Source of Antigen for Production of Immunosuppressive Antilymphocyte Serum"; 1973; pp. 541-547
Borella et al., J. of Immunology, 118(1), (1977), 309-315.
Barrett et al., Lancet, May 1, 1976, 940-941.
Levy et al., Proc. Natl. Acad. Sci., USA, 76(12), 1979, 6552-6556.
Schneider et al., Int. J. Cancer, 19, 621, 662, 652 & 626 (1977).

*Primary Examiner*—Howard E. Schain
*Attorney, Agent, or Firm*—Fleit, Jacobson, Cohn & Price

[57] ABSTRACT

Anti-T-lymphocyte globulin is prepared from the serum of immunized animals. Cells of the cell line JM are used for immunization. Anti-T-lymphocyte globulin is prepared by means of hybrid cells, which are obtained by a hybridization of myeloma cells capable of antibody synthesis with B-lymphocytes from animals or human beings. Said lymphocytes have a specificity against an antigen which is introduced. Cells of the cell line JM or their products are used as an antigen.

5 Claims, No Drawings

PREPARATION OF ANTI-T-LYMPHOCYTE GLOBULIN

CROSS-REFERENCE TO RELATED APPLICATIONS

This application is a continuation-in-part of application Ser. No. 347,502, filed Feb. 9, 1982, now abandoned.

This invention relates to the preparation of anti-T-lymphocyte globulin.

High-activity immunosuppressive drugs are used to suppress a rejection of the transplantate after an organ transplantation and to treat donor-to-host diseases after a bone marrow transplantation. Such drugs have previously been prepared in that lymphatic cells were injected into the body of an animal, such as a horse or rabbit, and the anti-lymphocyte globulin was recovered from the serum of the immunized animals. That process has the disadvantage that lymphatic cells are used, the procuring of which gives rise to ethical problems and which are available only in limited quantities.

It is an object of the invention to use cells grown in vitro for a preparation of immunosuppressive drugs.

The inventor has surprisingly found that an immunosuppressive drug having an excellent activity can be prepared with the aids of cells of the cell line JM. The production of the cell line JM and their properties have been described in the publication of U. Schneider, H. U. Schwenk and G. Bernkamm in Int. J. Cancer 19, 621–626 (1977). The cell line JM has been deposited under Number I 147 with the Institut Pasteur Collection Nationale der Culture des Microogranismes (C.N.C.M.). The cells can be grown in vitro as desired without losing their properties.

Another object of the invention is to produce anti-T-lymphocyte globulin in vitro. This is accomplished in accordance with the invention by the hybridization of myeloma cells capable of antibody synthesis, with B lymphocytes from animals or human beings, which lymphocytes have a specifity against the introduced antigen in the form of cells of the cell line JM or their products. Part of the hybrid cells thus formed continuously produce antibodies against the antigen. When these hybrid cells are separated, anti-T-lymphocyte globulin can be produced in vitro.

The method of cell hybridization has been described, e.g., by D. Gotze in "Immunforschung in Klinik und Labor", wissenschaftliche Information, Fresenius-Stiftung, special issue of August 1979, on page 5 et seq.

The immunizing B lymphocytes are preferably recovered from the lymphatic tissue of mice.

An example of a preparation of anti-T-lymphocyte globulin with the aid of the T-lymphoblast cell line JM will now be described.

The globulin is preferably prepared by the following steps:

PROCESS OF PREPARATION

I. Production of Antigens (Growing of Cells)

Lymphoblastoid T-cells (cell line JM) are grown as a suspended culture.

Nutrient: RPMI-1640 medium with additions of fetal calf serum, serum of neonatal calves, human serum, streptomycin-penicillin, L-glutamine.

Optimum temperature: 37° C.

Optimum pH value: 7.2 (phenol/red indicator).

Normal growth rate: The cell count is doubled in 48 hours. The cells are inspected every 48 hours. The cell count is adjusted to 0.5 million per ml.

The dead cell count should not exceed 10%.

Surplus cells are removed, centrifuged, washed and used for immunization.

Washing medium: Leibowitz Medium (L-15).

Immunizing dosage for one rabbit: $100 \times 10^6$ cells per 3 ml of medium.

Controlled Freezing of Cells for Immunization:

Any surplus cells which have been removed are washed three times with L-15 medium and after an addition of DMSO solution in a concentration of 10% are frozen at $-90°$ C. This is performed by automatic controlled freezing with a decrease of temperature of 1° C. per minute. For immunization, the frozen cells are thawed at 37° C. and are then washed immediately to remove the DMSO. Only fresh cells are used for the first immunization; frozen cells may be used for boosting.

Freezing of Cells for Subsequent Growing

Such cells are frozen in liquid nitrogen and are pretreated as described above before the they are frozen. In intervals of 3 to 4 months, part of such frozen cells is thawed for continued growing. This is necessary because the growing cell line may change the lose its surface T-antigen (this must be checked by the spontaneous rosette test).

Product of Medium

1. RPMI-1640 Medium

This medium has been published by Moore, G. E. et al, J.A.M.A. 199, 519 (1967).

The medium powder is prepared by Fresenius in Bad Homburg and supplied in aliquots for $1 \times 10$ liters of fluid medium (Dr. Kempf).

The powder is stored in a refrigerator.

The powder is dissolved in 10 liters Ampuwa (aqua ad injectionem) with an addition of 20 grams $NaHCO_3$. The pH value is adjusted to 7.05 (by an addition of 1N HCl). After stirring, the medium is subjected to a sterile filtration and filled into containers 500-ml (bottles).

The bottles are checked for sterility by incubation at 37° C. for 5 days.

The incubated bottles are then stored in a refrigerator at 6°–8° C.

2. L-15 Leibowitz Medium

This medium has been published by Leibowitz, A. et al, Am.J.Hyg. 78, 173 (1963) and used to suspend the cells for immunization.

The powder is obtained from Dynatech, Plochinger.

The powder is dissolved in 10 liters Ampuwa. The solution is subjected to sterile filtration and filled into 500-ml bottles.

Incubation; Storage in refrigerator.

II. Production of Antiserum

Immunization and Exsanguination of Rabbits

In accordance with the Order concerning Serums and Vaccines of Nov. 14, 1972 (Section 15), the animals are accommodated as follows:

First Hutch: Leased by FREESENIUS; at Gut Raucherberg, 8121 Wielenbach.

Supervising veterinarian: Dr. Thimel-Baumer of Fresenius AG

Supervising public veterinarian: Dr. Hanfstingl, State Veterinary Office, 8120 Weilheim
Autopsy: Tiergesundheitsdienst Bayern e.v., Senator Gerauerstrasse 23, 8011 Grub near Munich
Second Hutch: Dr. Ivanovas GmbH, Breeders of Experimental Animals, 7964 Kisslegg, Allgau.
Veterinarian: Dr. Albus.

Records on immunization, exsanguination and autopsy are prepared and kept.

The animals are immunized with cells of cell line JM.

First immunization: On the 1st day, intravenous injection.
  (into the ear vein) of 3 ml cell suspension (80 to $100 \times 10^6$ cells)

Second immunization: On the 14th day, as described above.

Third immunization: On the 17th day, as described above.

Exsanguination. On the 21st or 22nd day: Puncture of heart under anesthesia) p1 Anesthesia: By intravenous injection of 37 mg Nembutal per kg of body weight Puncture of heart: With K cannulas, 180/1.8
50 ml E-syringes
100-ml centrifuge beaker with screw cap The individual blood samples are kept at 4° C. overnight and are processed on the next day. The average quantity of blood taken is varied in dependence on the age and weight of the animals and amounts to 150 ml.

III. Production of Raw Serum

Further Processing of Individual Blood Samples

Centrifugation (at about 3000 g) for 15 minutes at 4°–8° C.
Siphoning the serum and second centriguation
Filling of individual samples into screw-capped bottles. Average yield about 70 ml per animal
Taking of samples for sterility and activity tests
Inactivation of serums at 56° C. in water bath for 30 minutes
Storage of individual samples at −18° C. until they are pooled
Intermediate tests (for sterility, activity)

Pooling

The individual serums of 250 to 300 animals are pooled in dependence on the result of the intermediate tests.
  Pool A: KBR titer against peripheral lymphocytes: 1:256 and more
  Pool B: KBR titer against peripheral lymphocytes: 1:64 to 1:128
  Pool C: KBR titer against peripheral lymphocytes: Less than 1:64

The hemagglutination titer is not in excess of 1:4000, as a rule.

Pools A and B are mixed so that the total titer is not less than 1:256. Pool C is discarded (10 to 20% of individual samples).

The pooled serums are filled into 500-ml bottles and are then stored at −18° C.

Intermediate Tests
  (a) Sterility test of each bottle
  (b) Test for KBR titer of pools A, B and C After the intermediate tests, the serum pool bottles are released for further processing.

IV. Preparation of Absorbents

Processing of Placenta

Fresh human placentas are obtained from the hospital and are kept in a frozen state until they are processed.

The frozen placenta is thawed gradually and is thoroughly washed with normal saline solution. The umbilical cord and fasciae are removed. A blood sample for the hepatitis test is taken from the umbilical cord. The placenta is divided and is mashed in a mixer. The homogenate is centrifuged (refrigerated centrifuge, 15 min at 3000 g) and is washed three times with normal saline solution and then filled into 500-ml bottles. A sample is taken for a bacteriological examination and is stored at −18° C. until the end of the intermediate tests:
  (a) Sterility test
  (b) Virus hepatitis test Erythrocyte Concentrate The washed, sterile erythrocyte concentrate is obtained from a blood bank, where it has been tested.

V. Further Processing of the Raw Serum Pool to the Final Product

1. Absorbents
(a) Absorption of Placenta

The thawed placenta homogenate is centrifuged and washed again. The sediment is weighed.

Proportions during absorption: 1 part placenta per 6 parts of serum.

The serum is poured over the placenta mash and both are shaken for ½ hour and are then centrifuged.

The supernatant liquor consisting of unabsorbed serum is removed and held ready for the next absorption.

A sample is taken for a direct hemagglutination. The titer is 1:512, as a rule.

(b) Absorption by Erythrocytes

The blood bag containing washed, sterile, fresh erythrocyte concentrate is obtained from the blood bank and is used immediately.

Two absorptions are carried out in proportions of 1 part erythrocytes per 5 parts serum.

The erythrocytes are carefully added to the serum. The mixture is shaken slowly and is incubated in a water bath at 37° C. for 1.5 hours while it is shaken every 10 minutes.

The mixture is then centrifuged for 15 minutes at 1000 r.p.m. in a refrigerated centrifuge.

The supernatant liquor is subjected to the absorption treatment once more.

The quantity of absorbed serum is about the same as the initial quantity of raw serum.

The hemagglutination titer is determined after each absorption and is between 1:128 and 1:64 after the first absorption and between 1:8 and 1:4 after the second absorption.

2. Precipitation With Ammonium Sulfate and Dialysis

The absorbed serum is mixed with an equal quantity of sterile, pyrogen-free water (Ampuva). Then a sterile saturated solution of $(NH_4)_2SO_4$ (adjustment with ammonia to pH 7.2) is added slowly by dripping at a ratio of 82 parts of ammonium sulfate solution per 100 parts of diluted serum. The precipitation is permitted to proceed overnight with stirring.

The precipitate is removed by centrifugation at 5000 to 6000 g for 30 minutes. The supernatant liquor is discarded. The precipitate is washed three times with ammonium sulfate solution having a concentration of 45%.

The final precipitate is dissolved together with one-half of the initial quantity of raw serum in Tris-HCl buffer solution having a pH value of 8.0 to 8.1. The solution is filled into dialysis sacks and dialyzed against Tris-HCl buffer solution. (24 hours, the buffer solution is replaced 4 times). The globulin fraction is then filled into 500-ml bottles and stored at −18° C. A sample is taken for the sterility test.

3. Ion Exchange Chromatography

The column is packed with cellulose and is equilibrated with Tris-HCl buffer solution. The hoses and hose couplings are autoclaved before. A sterile filter is connected before the inlet of the column.

The sample consisting of dialyzed globulin fraction is supplied by a pump and is then eluted with Tris-HCL buffer solution (pH value 8.0 to 8.1, 0.05M). The first peak representing IgG fraction contaminated with other immunoglobulin is collected and after an addition of sodium chloride solution having a concentration of 0.9% is concentrated.

4. Ultrafiltration

The first fraction obtained by the ion exchange is concentrated by ultrafiltration with a Diaflo Hollow Fiber Apparatus (Amicon) with a rejection limit of M.G. 50,000. The eluate is concentrated to a protein concentration of at least 25 mg/ml determination by spectrophotometer at 280 nm). The immunoglobulin yield is about 50% of the initial quantity. The highest loss is incurred during the column fractionation.

5. Dialysis, Ultracentrifugation, Sterile Filtration

After the ultrafiltration, the concentrate is filled into dialysis sacks and is dialyzed against a phosphate-buffered common salt solution, pH 7.0 (24 hours at 4° C.; the buffer solution is replaced four times).

To eliminate large complex molecules and fat molecules, the protein solution which has been dialyzed is centrifuged at 18,000 r.p.m. for 60 minutes at about 50,000 g.

The globulin solution is then subjected to a sterile filtration in a pressure vessel of steel under a pressure nitrogen atmosphere with a pleated membrane capsule having a pore width of 0.22 um and is subjected to a bubble point test. The globulin solution is subsequently adjusted to a protein content of 20 mg/ml, filled into 500-ml bottles and stored in a refrigerator until it is filled into smaller bottles. A sample is taken for the intermediate tests.

6. Bottling and Labeling

The globulin solution is filled into 5-ml and 10-ml serum bottles of glass, which are provided with rubber plugs and aluminum caps. These bottles are sterilized by being autoclaved immediately before they are filled. The filling apparatus is checked for contamination before the filling operation (pick-off plates, determination of airborne germs). The filling room is filled with formalin vapor in the night before the filling operation. The filling hoses are autoclaved.

Sterility tests: Sterilization test strip, autoclave treatment test strip, bio-indicators, temperature measurement.

Immediately before being bottled, the protein solution is subjected to another sterile filtration and is then filled into the bottles by means of the automatic filling apparatus (Perifill).

The rubber plugs and metal caps are applied by hand and fixed by means of a pneumatic crimping apparatus.

During the bottling operation, samples are taken for the final tests and a sample for readjustment is taken.

Labeling is effected manually at the present time. The introduction of an automatic labeling apparatus is intended.

The product is stored in a quarantine refrigerator at 4° C.

After the release, the product is kept in the storage refrigerator at 4° C.

Production States in Which Inspections are Made

I. Inspection of Cell Line
 Spontaneous rosette test for a quantitative determination of the T antigen.

II. Examination of Rabbits
 The animals are under veterinary supervision (by
 Dr. Thimel-Baumer) pursuant to Section 15 of the Order concerning Serums and Vaccines and after exsanguination are delivered to Tiergesundheitsdienst Bayern e.V. for autopsy.

III. Tests of Intermediate Products
 1. Individual Rabbit Serum Samples
  (a) Sterility test (bacteria, fungi)
  (b) Specific activity test (complement-fixing reaction)
  (c) Toxicity against human erythrocytes (direct hemagglutination)
 2. Absorbents
  (a) Placenta:
   1. Test for virus hepatitis (HbsAG-RIA), Pettenkofer-Institut
   2. Sterility test
  (b) Washed erythrocyte concentrate: Tests for virus hepatitis and sterility (by blood bank)
 3. Sterility test after precipitation with ammonium sulfate and dialysis
 4. In-vitro test for pyrogens (Pyrogent) before and after the column fractionation.

IV. Tests of Final Product Before Bottling
 1. Sterility test in accordance with Ph. Eur.
 2. Innocuousness test (Limulus test—Pyrogent)
 3. Activity
  Complement-fixing reaction
  Protein determination V. Tests of Final Product After Bottling (off-hand samples)
 1. Sterility test in accordance with Ph. Eur. (bacteriological testing laboratory of Fresenius AG, Bad Homburg)
 2. Test for viruses
  Examination of off-hand sample by Max-von-Pettenkofer-Institut, Munich
 3. Innocuousness test
  Pyrogenicity test on a rabbit (Ph. Eur.-bacteriological testing laboratory in Bad Homburg)
  Limulus test (Pyrogent)—Bad Homburg and Grafelfing
 4. Activity and identity tests
  Rosette inhibition
  Lymphotoxicity test (Institut für Hämatologie, Munich)
  Complement-fixing reaction
  Direct hemagglutination
  Immunoelectrophoresis
  Immunodiffusion

---

Polyacrylamine gel electrophoresis

-continued

| | |
|---|---|
| HPLC gel filtration | Institut fur Hamatologie |

Protein determination

Immunosuppressive property (skin transplantate survival time on monkeys: TNO Primates Center, Rijswijk)

ATG - Fresenius ®

(Anti-Human-T-Lymphocyte Globulin)

Methods of Inspection and Testing

1. Specification and Tests of Intermediate Products (In-process inspection)
   1.1 Individual rabbit serum samples
      (a) Sterility test (bacteria and fungi) in accordance with Ph. Eur.
      (b) Activity test (measurement of antibody titers against peripheral human lymphocytes in the complement-fixing reaction)
      (c) Toxicity against human erythrocytes determination of hemagglutinating antibodies by the direct hemagglutination test)
      Unsterile serums are discarded. The lower limit for the complement-fixing reaction is 1:64. Serums having lower values are discarded. An upper limit for the complement-fixing reaction need not be stated because the immunization with the JM cell line will not result in HV values above 1:4000.
   1.2 Rabbit Serum Pool
      Same tests as stated in 1.1 (a) to (c)
      Lower limit for complement-fixing reaction: 1:256.
   1.3 Absorbents
      (a) Placenta (blood from umbilical cord): Examination for virus hepatitis (HbsAG-RIA) by Pettenkofer-Institut, Munich
      (b) Placenta (mashed and washed): Sterility test in accordance with Ph. Eur.
      Virus-contaminated and insterile placentas are discarded.
      (c) Washed erythrocyte concentrate is examined for sterility and virus hepatits by the blood bank.
   1.4 Precipitated Serum
      After the precipitation with ammonium sulfate and the succeeding dialysis:
      (a) Sterility test in accordance with Ph. Eur.
      (b) The removal of the ammonium sulfate by dialysis is checked by an addition of nitric acid and barium chloride to a sample.
   1.5 Check of Cellulose before and after the column fractionation by a test of the eluate for pyrogens Limulus test - Pyrogent)
   1.6 Inspection of Final Product Before Bottling
      (a) Sterility test (bacteria and fungi)
      (b) In-vitro test for pyrogens (Limulus)
      (c) Complement-fixing reaction against peripheral lymphocytes
      (d) Photometric protein determination at 280 nm.
2. Specification and Inspection of Final Product (Final Inspection)
   2.1 Inspection for the General Properties of the Product to be Administered
      (a) Color: Colorless, clear as water to slightly opalescent
      (b) Odor: No specific odor
      (c) Visual inspection for suspended matter
      (d) pH value: 6.8 to 7.1
   2.2 Proof of Indentity and Determination of the Contents of Active Ingredients Rabbit Immunoglobulins
      (a) Immunoelectrophoresis against rabbit whole serum and against rabbit immunoglobulins
      (b) Polyacrylamide gel electrophoresis
      (c) HPLC gel filtration
      (d) Protein determination (by photometry, 280 nm, quotient 1.4), tolerance range for release ±10% protein.
   2.4 Activity Tests
      (a) Complement-fixing reaction
         Determination of antibody titers against peripheral human lymphocytes
         Lower limit 1:128, no upper limit
      (b) Rosette inhibition test
         Lower limit for 50% inhibition: 1:2000
      (c) Lymphocytotoxicity test
         Lower limit for 50% cytotoxicity: 1:2000
      (d) Direct hemagglutination
         Determination of hemagglutinating antibodies against human erythrocytes
   2.5 Inspection of Final Product for Purity
      (a) Test in accordance with Ph. Eur. II for bacteria and fungi
      (b) Test in accordance with Ph. Eur./1975 for pyrogens
      (c) Test for viruses (Pettenkofer-Institut)
      (d) Test for foreign proteins (Ouchterlony)
      (e) Test for antibodies against human serum (immunoelectrophoresis)
      (f) Test for antibodies against human thrombocytes (thrombocyte aggegation)

What is claimed is:

1. A process of preparing anti-T-lymphocyte globulin comprising:
   (a) culturing lymphoblastoid T-cells of the cell line JM;
   (b) in vivo production of antiserum; and
   (c) recovery of the anti-T-lymphocyte.
2. A process of preparing anti-T-lymphocyte globulin according to claim 3 wherein the in vivo production of antiserum comprises immunizing animals with the cell line JM.
3. A process of preparing anti-T-lymphocyte globulin comprising:
   (a) culturing lymphoblastoid T-cells of the cell line JM as a suspended culture;
   (b) in vivo production of antiserum, said production of antiserum comprising immunization of animals with said lymphoblastoid T-cells from (a);
   (c) exsanguination of said animals from (b) to recover blood containing anti-T-lymphocyte globulin;
   (d) centrifugation and pooling of said blood from (c) to recover raw serum containing anti-T-lymphocyte globulin;
   (e) absorption of said raw serum from (d) by placenta homogenate to produce a partially purified raw serum;
   (f) absorption of said partially purified raw serum from (e) by erythrocyte concentrate to produce more purified raw serum;
   (g) precipitation of said more purified raw serum from (f) with ammonium sulfate and dialysis of the resulting precipitate to produce a globulin fraction;
   (h) separation of an IgG fraction of said globulin fraction by ion exchange chromatography; and
   (i) purification of said IgG fraction from (h) to produce the anti-T-lymphocyte globulin.
4. The anti-T-lymphocyte globulin prepared by the process of claim 2.
5. A process according to claim 2 wherein the animals immunized with the cell line JM are rabbits.

* * * * *